(12) United States Patent
Plass et al.

(10) Patent No.: US 6,802,831 B2
(45) Date of Patent: Oct. 12, 2004

(54) OSTOMY COUPLING

(75) Inventors: Ron Plass, Lindfield (GB); Ian Whatley, London (GB)

(73) Assignee: Bristol-Myers Squibb Company, New York, NY (US)

(*) Notice: Subject to any disclaimer, the term of this patent is extended or adjusted under 35 U.S.C. 154(b) by 277 days.

(21) Appl. No.: 09/735,206

(22) Filed: Dec. 12, 2000

(65) Prior Publication Data

US 2001/0004687 A1 Jun. 21, 2001

(30) Foreign Application Priority Data

Dec. 13, 1999 (GB) .............................. 9929517

(51) Int. Cl.[7] .................................................. A61F 5/44
(52) U.S. Cl. ...................................... 604/332; 604/327
(58) Field of Search ................................ 604/332–345, 604/327

(56) References Cited

U.S. PATENT DOCUMENTS

| 4,460,363 A | * | 7/1984 | Steer et al. ................. 604/336 |
| 4,850,985 A | * | 7/1989 | Edwards et al. ............ 604/339 |
| 5,496,297 A | * | 3/1996 | Olsen ........................ 604/339 |
| 5,709,674 A | * | 1/1998 | Steer .......................... 604/342 |

FOREIGN PATENT DOCUMENTS

GB          2301533    * 12/1996 .......... A61F/5/448

* cited by examiner

*Primary Examiner*—John J. Calvert
*Assistant Examiner*—Michele Kidwell
(74) *Attorney, Agent, or Firm*—Stuart E. Krieger

(57) ABSTRACT

An ostomy coupling is described of the type comprising a locking member in the form of a resilient split ring, for fastening two ostomy coupling members together.

One feature of the invention is that one of the coupling members comprises a tapered seal seat surface for cooperating with a deflectable seal wing carried by the other member. The tapered seal seat has a smoothly curved taper, to enable a relatively large seal area to be provided within a low coupling profile height.

Another feature of one form of the invention is that the split ring has an inclined outer surface to form a smooth profile with the coupling member on which it is carried.

Another feature of another form of the invention is that each limb of the split ring is bifurcated to receive a radially projecting guide of the coupling member, on which the split ring is mounted. The split ring thus extends above and below the guide, removing the need for a mounting channel on the coupling member itself, and enabling the height of the coupling to be further reduced.

20 Claims, 4 Drawing Sheets

OSTOMY COUPLING

FIELD OF THE INVENTION

This invention relates to the field of ostomy products, and in particular to a coupling for releasably attaching an ostomy pouch to a pad or wafer worn on the body. The term "ostomy" is intended to be interpreted broadly, and includes colostomy, urostomy and ileostomy.

BACKGROUND TO THE INVENTION

The invention relates in particular to a type of ostomy coupling in which a deformable ring, for example, a split ring (or a ring which behaves substantially as a split ring) is used to fasten two coupling members together.

Such ostomy couplings are described for example in GB-A-2301533, GB-A-2299761 and EP-A-0737456.

The ostomy couplings described in these documents have proved to be extremely reliable, and yet easy to use. The resilient split ring can provide a secure mechanical fastening which is unlikely to come apart by accident; yet the fastening can be released when desired by simple manipulation of the split ring by finger, to enable the coupling members to be separated.

In addition, the couplings have excellent sealing characteristics, provided by a deflectable sealing wiper, which provides a large area axial seal over an annular band region. The seal performance is important because the human nose is extremely sensitive to the malodours within an ostomy pouch. If gases escape, for example, during physical movement while wearing the pouch, the odours can be extremely embarrassing for the wearer.

In general, seal performance may be affected by factors including manufacturing (moulding) tolerances; shrinkage of one or both of the coupling members during attachment to an adhesive wafer or to an ostomy pouch (after moulding); and bending or distortion of the coupling members while the ostomy pouch is being worn. For a deflectable seal, a relatively high sealing area is preferred to a so-called point seal, as this is able to accommodate wider variations to provide a reliable seal, in use.

Generally it is desirable for the coupling height to be a small as possible, so as to be comfortable and unobtrusive to wear. The minimum profile height of a split ring ostomy coupling is limited by a number of factors, including:

(a) The length of the deflectable seal, and the axial seal seat, required to provide a high sealing area (band), to achieve a reliable seal in use.

(b) The configuration of the coupling member profiles and the necessary material thicknesses, to support the split ring captively and movably on one of the coupling members, and to achieve a secure mechanical interlock between the coupling members.

SUMMARY OF THE INVENTION

Broadly speaking, a first aspect of the invention is to provide an ostomy coupling member comprising a curved seal surface acting as a seat for a deflectable seal of a complementary coupling member. By using a curved seal seat surface, a relatively large seal area can be provided in a small profile height.

In one form, an ostomy coupling member comprises a channel region, a first wall of the channel tapering in a curved taper towards the second wall such that the width of the channel narrows with a curved taper towards the channel floor.

Preferably, the channel is wider (at least at one point) than it is deep.

In one embodiment, the channel is substantially continuous (for example, annular or another closed loop shape). However, in an alternative embodiment, a segmented channel is used.

Preferably the channel, or at least the seal seat surface, is generally annular, although other closed loop shapes may be used as desired.

In another aspect, a coupling member comprises an annular seal having a curved configuration.

In another aspect, the invention provides an ostomy coupling comprising a first coupling member releasably securable to a second coupling member by means of a deformable coupling member behaving a split ring carried by one of the coupling members, the first coupling member comprising a seal seat surface which curves in a generally radial direction, and the second coupling member carrying a deflectable seal which, in use, bears against the curved seal seat when the coupling members are secured together.

In another aspect, the invention provides an ostomy coupling member having an annular channel extending radially inwardly from the side of the coupling member, the coupling member carrying a deformable ring or split ring received within the channel, wherein the ring or split ring is shaped to form a generally smooth (e.g. rounded or tapered) shape or contour transition with the coupling member.

Such a smooth contour is advantageous to avoid sharp edges of the coupling from being visible through the user's clothing, and to avoid sharp edges from possible catching on the wearer's clothes.

Preferably, the ring has a tapered or inclined outer surface. Preferably, the contour or profile of the coupling member with the ring mounted thereon is generally trapezoid.

Preferably, the ring comprises at least one projection (tab) for projecting through an aperture in the coupling member.

Preferably, the coupling member comprises a second channel, and the aperture or apertures communicate with the second channel.

Preferably, the ring is, or behaves substantially as, a split ring.

In another aspect, the invention provides a coupling member comprising at least one generally radially projecting guide, the coupling member carrying a deformable ring or split ring mounted on the guide, the ring (or split ring) having a channel means therein for receiving the guide, such that portions of the ring fit on either side of the guide to hold the ring captive on the guide.

Preferably, the ring is, or behaves substantially as, a split ring.

Preferably, each arm of the split ring is bifurcated to form the channel means.

The above aspects may be used independently. However, additional advantages can be achieved by using two or more of these aspects in combination. In particular, the preferred embodiments illustrate configurations of coupling members which can enable the height of a split ring coupling to be reduced without detracting from the excellent mechanical fastening and seal properties of the coupling.

BRIEF DESCRIPTION OF THE DRAWINGS

Non-limiting embodiments of the invention are now described, by way of example only, with reference to the accompanying drawings, in which.

DESCRIPTION OF PREFERRED EMBODIMENTS

Figure 1:
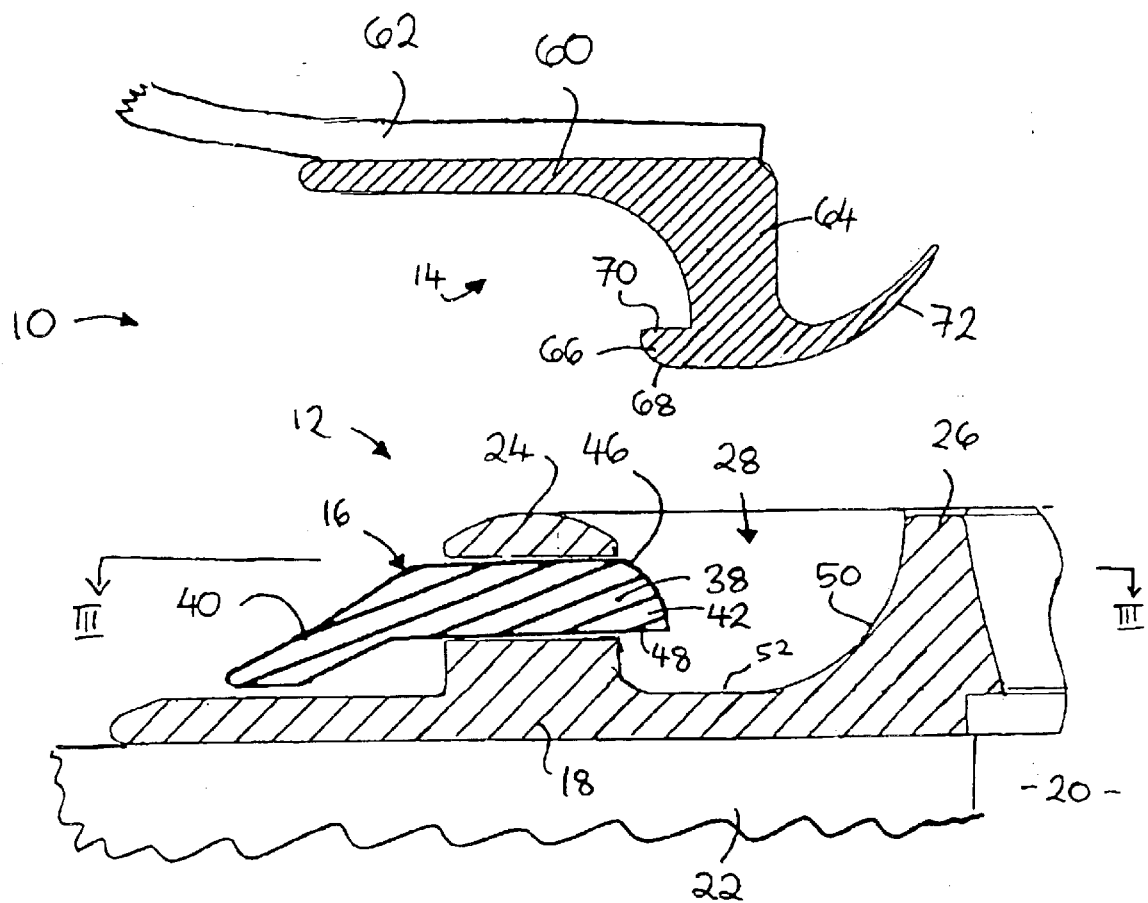
FIG. 1 is a sectional view through a first embodiment of ostomy coupling.
Figure 2:
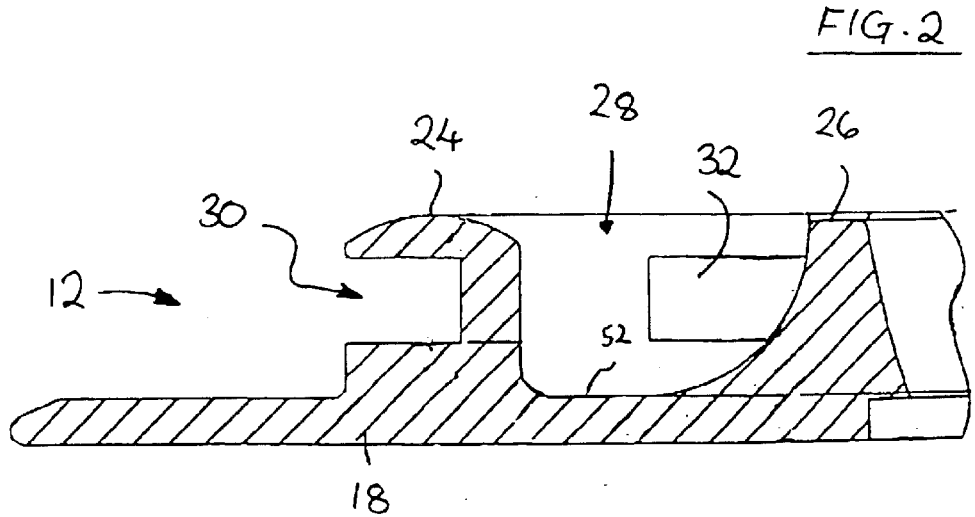
FIG. 2 is a sectional view through the bodyside coupling member of the coupling of FIG. 1 in isolation at an angular position offset from that of FIG. 1.
Figure 3:
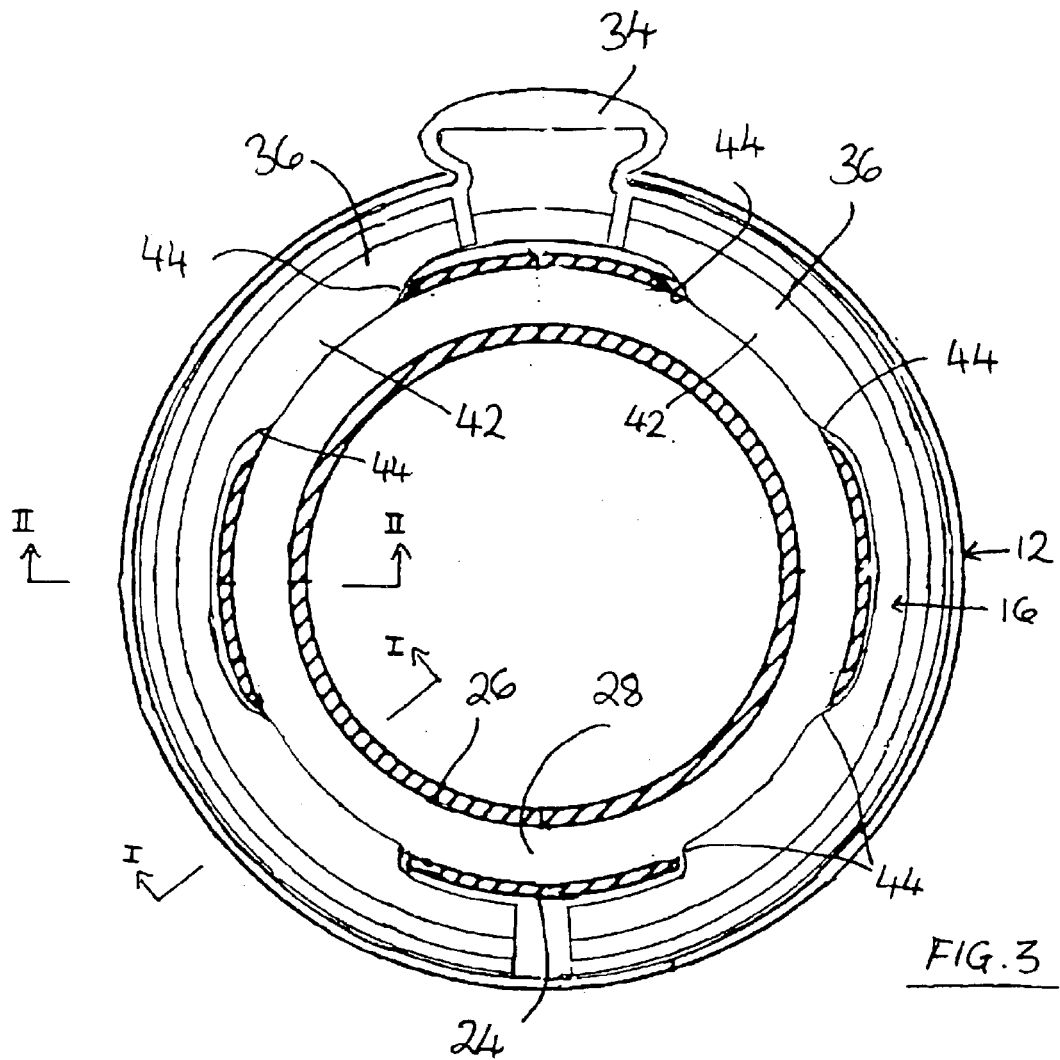
FIG. 3 is a sectional view along the line III—III of FIG. 1 (in FIG. 3, the line II—II indicates the corresponding section line for FIG. 2)

Referring to FIGS. 1–4, an ostomy coupling 10 comprises a plastics bodyside coupling member 12 and a plastics bagside coupling member 14, which are securable together by means of a resilient split ring 16 carried by the bodyside member 12. Although the embodiment is described in its preferred form in which the split ring 16 is carried by the bodyside member 12, it will be appreciated that the two members may be swapped as desired, such that the split ring 16 is carried on the bagside.

The bodyside member 12 comprises an annular flange 18 surrounding an aperture 20, and secured to an adhesive pad or wafer 22. Any suitable skin adhesive may be used, and such adhesives are well known to the skilled man.

Projecting from the flange 18 are concentric cylindrical walls 24 and 26 defining an annular channel 28 therebetween. The outer cylindrical wall, or outer wall, 24 is formed with a radially outwardly facing annular clearance or partial recess 30 (best seen in FIG. 2) which communicates with the channel 28 through a plurality of spaced apart slots 32 through the outer wall 24.

The split ring 16 is received within the annular recess 30. The split ring 16 comprises a handle region 34 from which extend two arcuate limbs 36. The limbs 36 each consist generally of a radially inwardly facing planar portion 38 from which depends a radially outwardly facing skirt portion 40. The skirt portion 40 is inclined, or tapered, to provide a generally smooth shape which blends in to the shape of the bodyside member 12, and generally provides a smooth, gradual, profile transition between the upstanding outer wall 24 and the peripheral region of the flange 18. The overall profile of the bodyside coupling member 12 carrying the split ring 16 is generally trapezoid.

Such a smooth shape is advantageous in making the coupling less obtrusive through the wearer's clothing, and in reducing any risk of the coupling catching on clothing.

Projecting from the radially inner edge of the split ring 16 are a number of locking tabs 42 which, when the ring 16 is in a central position on the bodyside member 12 (illustrated in FIG. 3), project through the slots 32 into the channel 28 for locking the coupling members together (as described further below). The circumferential ends 44 of the tabs 42 are tapered, or rounded, and the corresponding edges of each slot are also rounded or tapered with a generally complementary profile. In use, when a rotational force is applied to the handle 34 of the split ring 16 tending to rotate the split ring 16, the tapered ends 44 of the tabs 42 slide against the confronting edges of the slots with a camming action, to withdraw, or retract, the tabs 42 at least partly from the channel 28.

As best seen in FIG. 1, the upper edge 46 of each tab 42 (as viewed in FIG. 1) is rounded or tapered to provide a snap-together function of the coupling (as described further below). The lower edge 48 has a more square locking profile for locking the bagside coupling member 14 within the channel 28 until the split ring 16 is deformed to withdraw the tabs 42 in the manner described above.

The seal seat surface 50 of the inner cylindrical wall, or inner wall, 26 which faces the outer wall 24 curves towards the outer wall 24 such that the channel 28 narrows in width towards the channel floor 52. The seal seat surface 50 acts as a curved (tapered) seal seat for the seal of the bagside coupling member 14 when the two members are fastened together. At at least an upper part of the channel 28, the channel is wider than it is deep.

The bagside coupling member 14 comprises a generally annular flange 60 secured (for example, welded) to a wall 62 of an ostomy pouch, to surround its entry aperture. Projecting from the flange 60 is a generally cylindrical rib 64 dimensioned to fit within the channel 28 of the bodyside member 12. The rib 64 has an annular undercut projection 66 on its radially outer edge, for co-operating with the locking tabs 42 of the split ring 16. In a similar manner to the tabs 42, the projection 66 has a rounded or tapered leading edge 68, and a more square rear locking surface 70.

On its radially inner face, the rib 64 carries an integrally moulded deflectable seal wing 72 for bearing against the seal seat surface 50 of the bodyside member 12. The deflectable seal 72 has a generally curved shape, and tapers in thickness towards its free end. In its natural condition, the seal 72 is generally less curved than the seat surface 50, such that the seal 72 is somewhat "oversize" and has to deflect at least to some degree when entering the channel 28.

Figure 4:
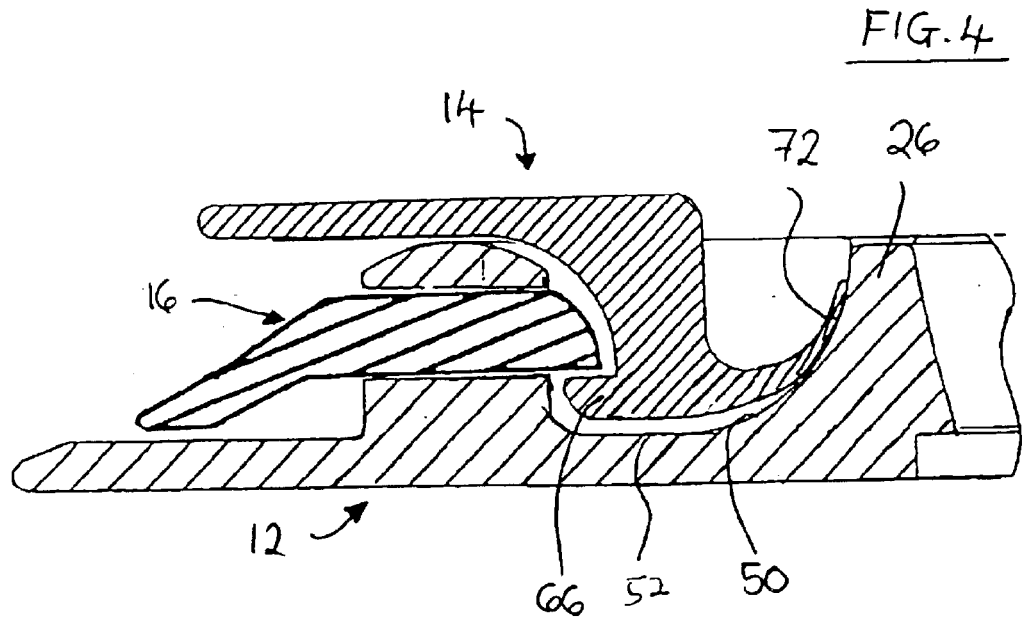
FIG. 4 is sectional view similar to FIG. 1, but showing the coupling members fastened together.
Figure 5:
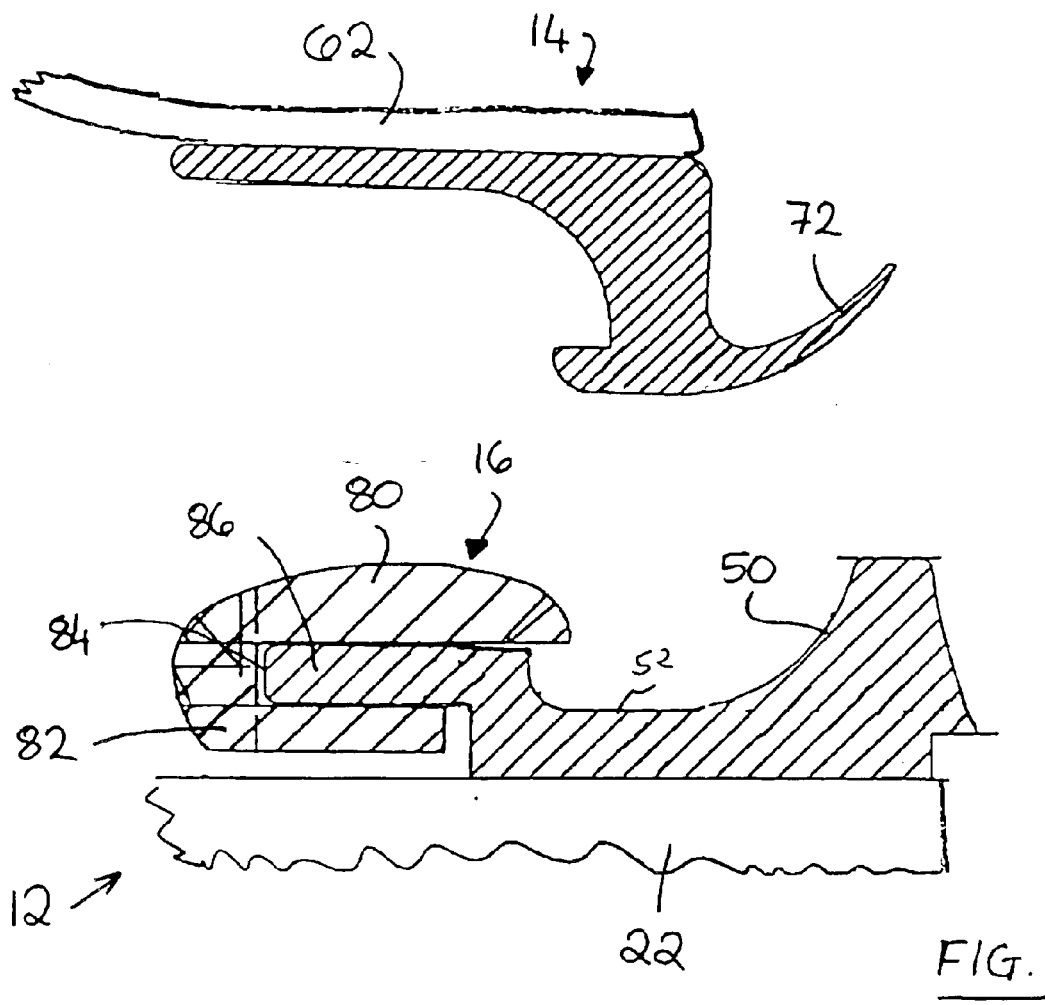
FIG. 5 is a sectional view through a second embodiment of ostomy coupling.
Figure 6:
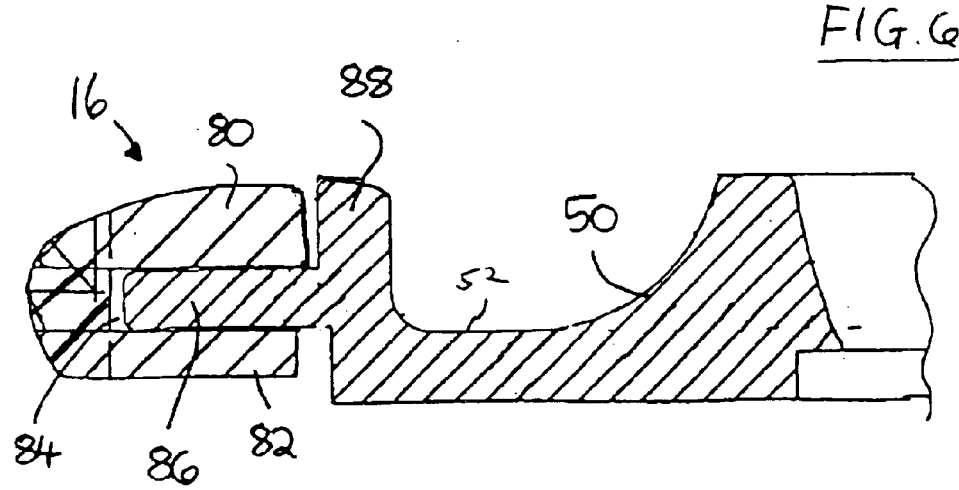
FIG. 6 is a sectional view through the bodyside coupling member of the coupling of FIG. 5 in isolation at an angular position offset from that of FIG. 5.
Figure 7:
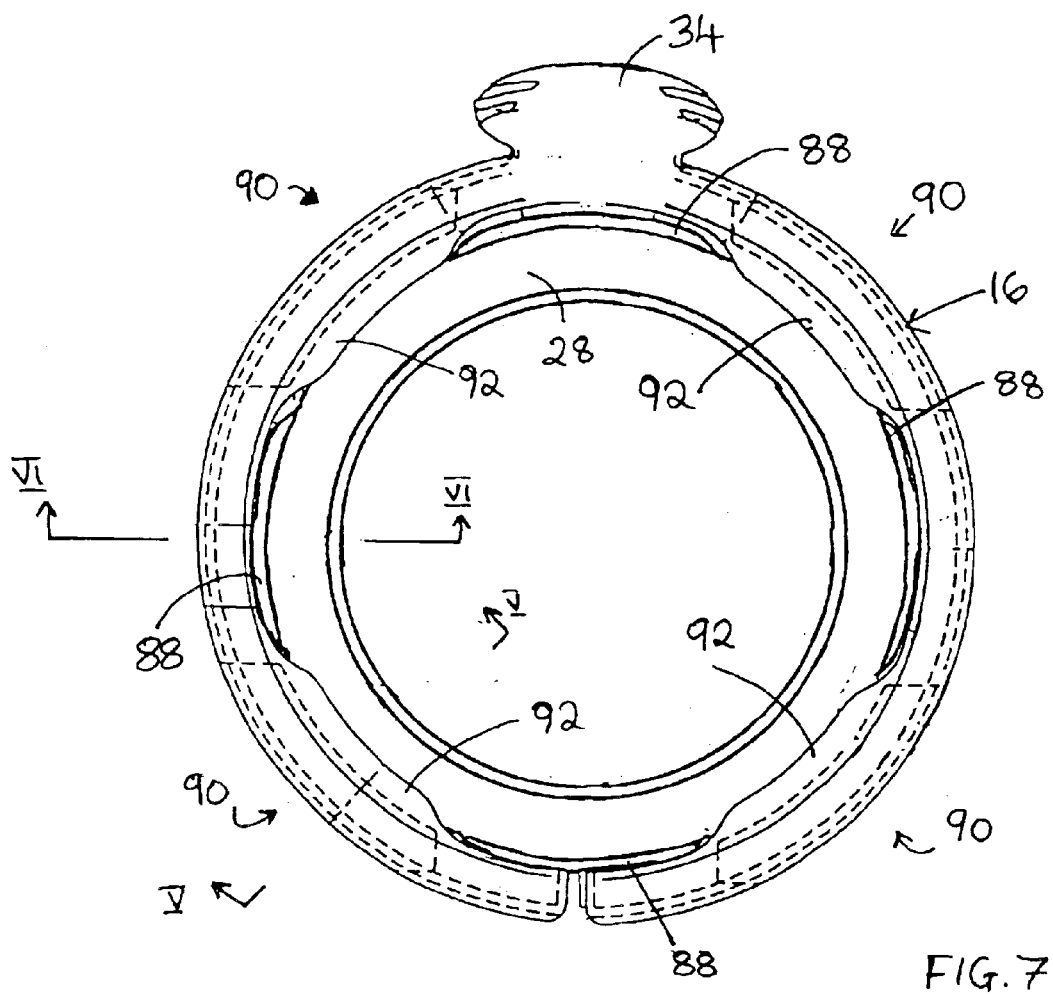
FIG. 7 is a plan view of the bodyside coupling member of FIG. 5 (in FIG. 7, the lines V—V and VI—VI represent the respective positions of the views of FIGS. 5 and 6)
Figure 8:
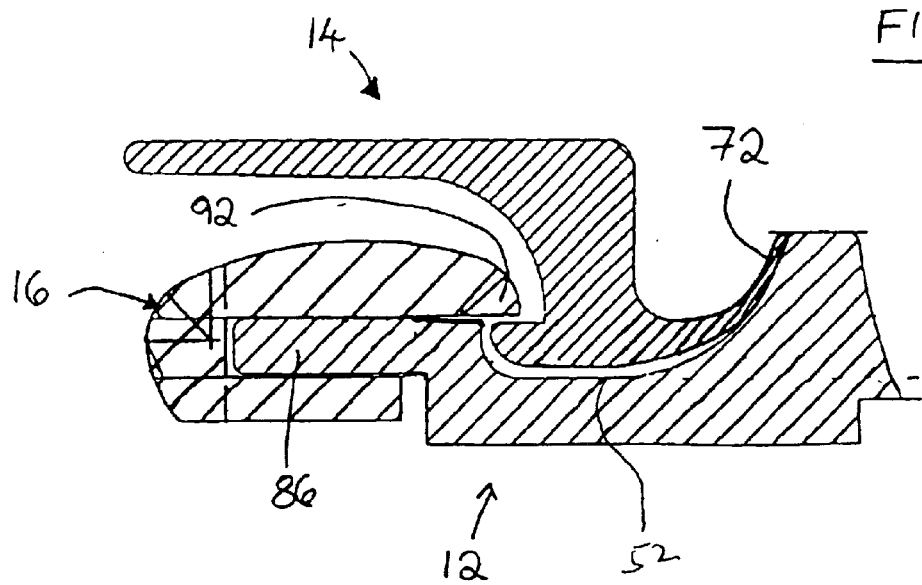
FIG. 8 is a sectional view similar to FIG. 5, but showing the coupling members fastened together.

In use, to fasten the coupling members 12 and 14, it is necessary simply to press the bagside member 14 against the bodyside member 12 with the rib 64 in register with the channel 28 (FIG. 1). The rounded leading edge 68 of the projection 66 bearing against the rounded upper edges 46 of the tabs 42 urges the tabs 42 outwardly, causing the split ring 16 to expand, to permit the projection 66 to enter fully into the channel. Referring to FIG. 4, once the projection 66 has passed the tabs 42, the split ring 16 snaps back to its original shape, causing the tabs 42 to engage behind the projection 66, and thereby lock the rib 64 within the channel 28. This provides a detectable "snap" or "click" which assures the wearer that the coupling members are securely fastened together.

As best seen in FIG. 4, in the assembled condition of the coupling members 12 and 14, the deflectable seal 72 is deflected to bear against the more curved seal seat surface 50 of the inner wall 26. Generally, the seal 72 is deflected to form a contact region in the form of an annular band (i.e. extending over a range of axial positions), rather than a so-called annular point seal. As explained previously, such a band seal is extremely advantageous in providing an effective seal in use, even when the coupling is subjected to distortions (for example, caused by physical movement of the wearer).

The use of a curved sealing seat, and a curved deflectable seal, enables a relatively long deflectable seal to be used within a reduced profile height (compared to an axial seal seat). This can enable the excellent performance of the axial seal seat to be used in a reduced height coupling profile, Typically, with such a design, it is possible to reduce the profile height of the bodyside coupling to about 4.5 mm (or even less), which might in some circumstances be difficult to achieve using a purely axial seal.

Referring now to FIGS. 5–8, a second embodiment of ostomy coupling is now described. This is similar in many respects to the first embodiment, and where appropriate the same reference numerals are used to denote the same features as those of the first embodiment.

In the second embodiment, the bagside coupling member 14 is identical to that of the first embodiment. Also, the bodyside coupling member 12 employs the same curved seal seat surface 50, to enable a relative large sealing surface to be accommodated within a relatively low profile height, without reducing the seal performance.

The main difference in the second embodiment lies in the design of the split ring 16, and the manner in which it is mounted on the bodyside coupling member 12. In the second embodiment, the split ring 16 is bifurcated to have an approximately U-shaped cross section, including upper and lower portions 80 and 82, respectively above and below an annular clearance 84. Instead of being received within an annular recess, the split ring 16 is carried on a radially projecting flange 86 of the bodyside coupling member 12. The flange 86 is received within the clearance 84 of the split ring 16, and the upper and lower portions 80 and 82 hold the split ring 16 captive on the flange 86.

In the second embodiment, the outer cylindrical wall 24 is replaced by a plurality of wall segments 88 spaced apart by spaces 90 equivalent to the slots 32 of the first embodiment. The upper portion 80 of the split ring 16 carries locking tabs 92 equivalent to the locking tabs 42 of the first embodiment. When the split ring 16 is in its central position (FIG. 7), the tabs 92 project through the spaces 90 to engage the bagside coupling member 14 in the same manner as the first embodiment.

The circumferential ends of the tabs 92, and the corresponding end surfaces of the wall segments 88, are tapered or rounded to cause the tabs 92 to be withdrawn when a force is applied to the handle 34 of the split ring 16 tending to rotate the split ring 16. The upper edges of the tabs 92 are also rounded or tapered to provide a snap-fit with the bagside coupling member 14. The split ring 16 thus functions in the same manner as in the first embodiment.

In the second embodiment, the height of the wall segments 88 can be less than the height of the outer wall 24 of the first embodiment. It is preferred that the wall segments 88 are only about as high as the upper region 82 of the split ring 16, so that the wall segments 88 are generally flush with the upper surface of the split ring 16. Typically, with such a design, it is possible to reduce the profile height of the bodyside coupling member to about 3.8–3.9 mm (or even less), which may be even lower than the first embodiment.

It will be appreciated that the foregoing description is merely illustrative of preferred embodiments of the invention. The skilled man will be aware of many possible variations and equivalents within the scope and spirit of the invention.

What is claimed is:

1. An ostomy coupling fastenable by a deformable locking member, the coupling comprising:
    a first coupling member comprising a deflectable seal wing extending around a coupling aperture of the first coupling member;
    a second coupling member comprising a seal seat surface extending around a coupling aperture of the second coupling member, the seal seat surface tapering with a curved taper in a direction towards the first coupling member when the coupling members are in an assembled condition; and
    a deformable split ring locking member being carried on one of the coupling members for releasably fastening the coupling members together, said deformable split ring locking member being deformable so as to expand upon pushing said first and second coupling members together into an assembled condition and thereafter resiliently contract for locking said assembled first and second coupling members together, said assembled members being separable upon expansion of said locking ring;
    wherein, in use, when the coupling members are in said assembled condition, the deflectable seal wing is deformed into a curvature to bear against the curved taper of the seal seat surface so as to form a seal.

2. An ostomy coupling according to claim 1, wherein the seal seat surface curves about 90 degrees.

3. An ostomy coupling according to claim 2, wherein the seal seat surface curves from a first direction generally parallel to a plane of the second coupling member to a second direction generally perpendicular to said plane.

4. An ostomy coupling according to claim 1, wherein the seal seat surface curves generally uniformly over a major portion of the seal seat surface.

5. An ostomy coupling according claim 1, wherein the deflectable seal wing is curved in the same direction as the seal seat surface, the deflectable seal wing having less curvature than the seal seat surface whereby when the deflectable seal wing bears against the seal seat surface when the coupling members are assembled together, the seal wing is deformed into a more curved shape.

6. An ostomy coupling member for releasable attachment to a second ostomy coupling part, the ostomy coupling member comprising:
    a guide for a locking member;
    a deformable split ring locking member movably supported by said guide, and having a plurality of locking projections, the locking member being expandable to move the locking projections outwardly by rotation of the locking member relative to the guide, said locking member being expandable upon pushing said ostomy coupling member and second ostomy coupling part together into an assembled condition and thereafter resiliently contract for locking said assembled ostomy coupling member and ostomy coupling part together, said assembled members being separable upon expansion of said locking member; and
    a seal seat surface extending around an aperture of the coupling member and facing the deformable locking member, the seal seat surface tapering with a curved taper in a direction generally perpendicular to the plane of the locking member, there being a clearance between the seal seat surface and one of the guide and the locking member for receiving the second ostomy coupling part.

7. An ostomy coupling fastenable by a deformable locking member, the coupling comprising:
    a first coupling member comprising a rib carrying a deflectable seal wing;
    a second coupling member comprising first and second walls defining at least one channel portion for receiving at least part of the rib, said channel portion having a channel floor, the first wall defining a seal seat for the deflectable seal wing and tapering in a curved taper towards the second wall such that the width of the channel portion narrows with a curved taper towards the channel floor; and a deformable split ring locking member being carried on one of the coupling members for releasably fastening the coupling members together, said deformable split ring locking member being deformable so as to expand upon pushing said first and second coupling members together into an assembled condition and thereafter resiliently contract for locking said assembled first and second coupling members together, said assembled members being separable upon expansion of said locking member.

8. An ostomy coupling according to claim 7, wherein the channel portion is wider at least at one point than the channel portion is deep.

9. An ostomy coupling according to claim 7, wherein the channel portion is substantially continuous.

10. An ostomy coupling according to claim 7, wherein the channel portion and the rib each have a generally annular shape.

11. An ostomy coupling according to claim 7, comprising a plurality of spaced apart channel portions defining spaced channel segments.

12. An ostomy coupling according claim 7, wherein the deflectable seal wing is curved in the same direction as the seal seat surface, the deflectable seal wing having less curvature than the seal seat surface whereby when the deflectable seal wing bears against the seal seat surface when the coupling members are assembled together, the seal wing is deformed into a more curved shape.

13. An ostomy coupling member for releasable attachment to a second ostomy coupling part, the ostomy coupling member comprising:

first and second walls defining at least one channel portion for receiving the second coupling part, the channel portion having a width and a floor, the first wall tapering in a curved taper towards the second wall such that the width of the channel narrows with a curved taper towards the channel floor;

a deformable split ring locking member movably mounted around the second wall and carrying a plurality of locking projections which project through or around the second wall towards the tapering of the first wall, said locking member being expandable upon pushing said ostomy coupling member and second ostomy coupling part together into an assembled condition and thereafter resiliently contract for locking said assembled ostomy coupling member and ostomy coupling part together, said assembled members being separable upon expansion of said locking member;

wherein the locking member is expandable by rotation of the locking ring relative to the second wall to cause the locking projections to move outwardly away from the first wall.

14. An ostomy coupling member for releasable attachment to a second ostomy coupling part, the ostomy coupling member comprising:

a flange from which upstands an annular wall having radially inner and outer surfaces, the radially outer surface being formed with an annular clearance, a deformable split ring locking member received by the annular clearance, said locking member being expandable upon pushing said ostomy coupling member and second ostomy coupling part together into an assembled condition and thereafter resiliently contract for locking said assembled ostomy coupling member and ostomy coupling part together, said assembled members being separable upon expansion of said locking member;

wherein the flange extends radially outwardly of the annular wall, and the deformable locking member has an inclined outer face to form a generally inclined profile shape between the flange and the annular wall.

15. An ostomy coupling member according to claim 14, wherein the deformable locking member forms a generally smooth profile shape between the flange and the annular wall.

16. An ostomy coupling member according to claim 14 having a vertical profile, wherein the profile of the coupling member with the deformable locking member carried thereon has a vertical profile and said profile is generally trapezoidal.

17. An ostomy coupling member according to claim 14, wherein ostomy coupling member further comprises an annular channel for receiving the second coupling part, the annular channel communicating with the annular clearance through a plurality of apertures.

18. An ostomy coupling member for releasable attachment to a second ostomy coupling part, the ostomy coupling member comprising:

a generally radially projecting guide; and a deformable split ring locking member mounted movably on the guide, said locking ring being expandable upon pushing said ostomy coupling member and second ostomy coupling part together into an assembled condition and thereafter resiliently contract for locking said assembled ostomy coupling member and ostomy coupling part together, said assembled members being separable upon expansion of said locking member;

wherein the deformable split ring locking member comprises first and second limbs, each limb comprising respective upper and lower projections with a clearance therebetween, the guide being received within the clearance and the upper and lower portions fitting above and below the guide to retain the locking member thereon.

19. An ostomy coupling member according to claim 18, wherein each limb of the split ring is bifurcated.

20. An ostomy coupling member according to claim 18, wherein the deformable locking ring member comprises a plurality of locking projections, and wherein the coupling member further comprises a plurality of wall segments, the locking projections projecting through spaces between adjacent wall segments.

* * * * *